US006582934B2

(12) United States Patent
Majumdar (10) Patent No.: US 6,582,934 B2
(45) Date of Patent: Jun. 24, 2003

(54) RECOMBINANT DNA ENCODING AN EPIDERMAL GROWTH FACTOR RECEPTOR RELATED PROTEIN

(75) Inventor: Adhip P. N. Majumdar, W. Bloomfield, MI (US)

(73) Assignees: The United States of America as represented by the Department of Veterans Affairs, Washington, DC (US); Wayne State University, Detroit, MI (US)

( * ) Notice: Subject to any disclaimer, the term of this patent is extended or adjusted under 35 U.S.C. 154(b) by 0 days.

(21) Appl. No.: 09/867,521

(22) Filed: May 31, 2001

(65) Prior Publication Data

US 2002/0045215 A1 Apr. 18, 2002

Related U.S. Application Data

(62) Division of application No. 09/570,454, filed on May 12, 2000, now Pat. No. 6,399,743.

(51) Int. Cl.[7] ............................ C12N 15/00; C07H 21/04
(52) U.S. Cl. ................ 435/69.1; 435/320.1; 435/252.3; 435/325; 435/6; 536/23.5
(58) Field of Search ................ 435/69.1, 320.1, 435/252.3, 325, 366, 6; 536/23.1

(56) References Cited

U.S. PATENT DOCUMENTS

| | | | |
|---|---|---|---|
| 5,550,214 A | 8/1996 | Eberlein et al. ............ 530/328 |
| 5,578,482 A | 11/1996 | Lippman et al. .......... 435/240.1 |
| 5,635,399 A | 6/1997 | Kriegler et al. .......... 435/320.1 |
| 5,641,484 A | 6/1997 | Hung et al. ................ 424/93.2 |
| 5,643,567 A | 7/1997 | Hung et al. ................ 424/93.2 |
| 5,650,415 A | 7/1997 | Tang et al. ................. 514/312 |
| 5,651,964 A | 7/1997 | Hung et al. ................ 424/93.2 |
| 5,652,130 A | 7/1997 | Kriegler et al. ............ 435/366 |
| 5,677,171 A | 10/1997 | Hudziak et al. ....... 435/240.27 |
| 5,693,522 A | 12/1997 | Chada et al. .............. 435/402 |
| 5,700,822 A | 12/1997 | Hirth et al. ................ 514/380 |
| 5,710,173 A | 1/1998 | Tang et al. ................. 514/447 |
| 5,720,937 A | 2/1998 | Hudziak et al. ........... 424/9.34 |
| 5,721,277 A | 2/1998 | Tang ........................... 514/646 |
| 5,725,856 A | 3/1998 | Hudziak et al. ........... 424/130.1 |
| 5,760,066 A | 6/1998 | Tang ........................... 514/378 |
| 5,763,470 A | 6/1998 | Tang et al. ................. 514/406 |
| 5,770,195 A | 6/1998 | Hudziak et al. ........... 424/130.1 |
| 5,772,997 A | 6/1998 | Hudziak et al. ........... 424/130.1 |
| 5,773,459 A | 6/1998 | Tang et al. ................. 514/445 |
| 5,773,476 A | 6/1998 | Chen et al. ................. 514/620 |
| 5,789,427 A | 8/1998 | Chen et al. ................. 514/352 |
| 5,792,783 A | 8/1998 | Tang et al. ................. 514/397 |
| 5,804,396 A | 9/1998 | Plowman .................... 435/7.23 |
| 5,807,989 A | 9/1998 | Margolis et al. ............ 530/350 |
| 5,814,315 A | 9/1998 | Hung et al. ................ 424/93.2 |
| 5,814,630 A | 9/1998 | Barker et al. .............. 514/234.5 |
| 5,821,246 A | 10/1998 | Brown et al. ............... 514/253 |
| 5,834,504 A | 11/1998 | Tang et al. ................. 514/418 |
| 5,837,510 A | 11/1998 | Goldsmith et al. ........ 435/172.3 |
| 5,837,523 A | 11/1998 | Greene et al. .............. 435/320.1 |
| 5,849,586 A | 12/1998 | Kriegler et al. ............ 435/372 |
| 5,856,089 A | 1/1999 | Wang et al. ................ 435/6 |
| 5,861,290 A | 1/1999 | Goldsmith et al. ........ 435/172.3 |
| 5,863,797 A | 1/1999 | Kriegler et al. ............ 435/366 |
| 5,869,445 A | 2/1999 | Cheever et al. ............ 514/2 |
| 5,869,618 A | 2/1999 | Lippman et al. .......... 530/387.1 |
| 5,874,077 A | 2/1999 | Kriegler et al. ........... 424/93.21 |
| 5,880,141 A | 3/1999 | Tang et al. ................. 514/339 |
| 5,883,113 A | 3/1999 | Tang et al. ................. 514/418 |
| 5,883,116 A | 3/1999 | Tang et al. ................. 514/418 |
| 5,886,020 A | 3/1999 | Tang et al. ................. 514/418 |
| 5,888,965 A | 3/1999 | Kmiecik et al. ............ 514/2 |
| 5,889,156 A | 3/1999 | Kriegler et al. ............ 530/351 |
| 5,891,917 A | 4/1999 | Tang et al. ................. 514/604 |
| 5,914,343 A | 6/1999 | Tang ........................... 514/398 |
| 5,932,574 A | 8/1999 | Baker ........................ 514/234.5 |
| 5,932,602 A | 8/1999 | Hirth et al. ................ 514/380 |
| 5,935,993 A | 8/1999 | Tang et al. ................. 514/445 |
| 5,942,514 A | 8/1999 | Barker ........................ 514/259 |
| 5,955,464 A | 9/1999 | Barker ........................ 514/259 |
| 5,958,959 A | 9/1999 | Hirth et al. ................ 514/378 |
| 5,962,458 A | 10/1999 | Lohmann et al. .......... 514/259 |

(List continued on next page.)

OTHER PUBLICATIONS

Aviv et al. Comparison of EGF receptor sequences as a guide to study the ligand binding site. 1991. Oncogene, 6(4):673–76.*

Ullrich et al., Signal Transduction by Receptors with Tyrosine Kinase Activity, Cell, vol. 61, pp. 203–212, 1990.

Reiter et al., A 1.8 kb alternative transcript from the human epidermal growth factor receptor gene encodes a truncated form of the receptor, Nucleic Acids Research, 1996, vol. 24, No. 20, pp. 4050–4056.

(List continued on next page.)

*Primary Examiner*—Lorraine Spector
*Assistant Examiner*—Dong Jiang
(74) *Attorney, Agent, or Firm*—Blank Rome LLP (57) ABSTRACT

A cDNA fragment clone of 1583 base pairs with 90–95% sequence homology to the mouse EGFR and a truncated rat EGFR is described. The isolated cDNA is termed ERRP (EFG-Receptor Related Protein). In Northern-blot analysis with poly A+RNA from different rat tissues, ERRP cDNA hybridized strongly to a mRNA transcript of about 1.8 kb. Maximal expression was noted in the small intestine, followed by colon, liver, gastric mucosa and other tissues. Transfection of ERRP cDNA in HCT-116 cells, a colon cancer cell line, markedly inhibits proliferation in monolayer and in soft agar and attenuates EGF-R tyrosine kinase activity. Transfection of ERRP in HCT-116 also delays tumor growth in SCID mice injected with these cells compared to the vector-transfector control cells. On the other hand, proliferation of the vector-transfected control, but not ERRP transfected HCT cells could be stimulated by TGF-α ($10^{-10}$M and $10^{-9}$M). The ERRP cDNA represents a new member of the EGFR gene family, and its protein product plays a key role in modulating the function of EGFR.

12 Claims, 9 Drawing Sheets

U.S. PATENT DOCUMENTS

| | | | | |
|---|---|---|---|---|
| 5,972,639 | A | 10/1999 | Parandoosh | 435/29 |
| 5,977,102 | A | 11/1999 | Himmelsbach et al. | 514/234.2 |
| 5,985,553 | A | 11/1999 | King et al. | 435/6 |
| 5,990,141 | A | 11/1999 | Hirth et al. | 514/378 |
| 5,997,859 | A | 12/1999 | Barber et al. | 424/93.2 |
| 5,998,136 | A | 12/1999 | Kamb | 435/6 |
| 6,015,567 | A | 1/2000 | Hudziak et al. | 424/277.1 |
| 6,015,814 | A | 1/2000 | Barker | 514/259 |
| 6,040,290 | A | 3/2000 | Lippman et al. | 514/12 |
| 6,051,593 | A | 4/2000 | Tang et al. | 514/397 |
| 6,071,512 | A | 6/2000 | Kriegler et al. | 424/93.21 |
| 6,071,921 | A | 6/2000 | Lohmann et al. | 514/259 |

OTHER PUBLICATIONS

Margolis et al., EGF Induces Tyrosine Phosphorylation of Phospholipase C–II: A potential Mechanism for EGF Receptor Signaling, Cell vol. 57, pp. 1101–1107, 1989.

Kypta et al., Association between the PDGF Receptor and Members of the src Family of Tyrosine Kinases, Cell, vol. 62, pp. 481–492, 1990.

Otsu et al., Characterization of Two 85 kd Proteins that Associate with Receptor Tyrosine Kinases, Middle–T/ $pp60^{c-src}$ Complexes, and PI3–Kinase, Cell, vol. 65, pp. 91–104, 1991.

Skolnik et al., Cloning of PII3 Kinase–Associated p85 Utilizing a Novel Method for Expression/Cloning of Target Proteins for Receptor TyrosineKinases, Cell, vol. 65, pp. 83–90, 1991.

Escobedo et al., cDNA Cloning of a Novel 85 kd Protein that has $SH_2$ Domains and Regulates Binding of PI3–Kinase to the PDGF β–Receptor, Cell, vol. 65, pp. 75–92, 1991.

Kazlauskas et al., Autophosphorylation of the PDGF Receptor in the Kinase Insert Region Regulates Interactiosn with Cell Proteins, Cell, vol. 58; 1121–1131, 1989.

Kaplan et al., PDGF β–Receptor Stimulates Tyrosine Phosphorylation of GAP and Association of GAP with a Signalling Complex.

Morrison et al., Direct Activation of the Serine/Threonine Kinase Activity of Raf–1 through Tyrosine Phosphorylation by the PDGF β–Receptor, Cell, vol. 58, pp. 649–657, 1989.

Meisenhelder et al., Phospholipase C–y Is a Substrate for the PDGF and EGF Receptor Protein–Tyrosine Kinases In Vivo and In Vitro, Cell, vol. 57, pp. 1109–1122, 1989.

Ruderman et al., Activation of phosphatidylinositol 3–kinase by insulin, Proc. Natl. Acad. Sci., USA, vol. 87, pp. 1411–1415, 1990, Cell Biology.

Kazlaukas et al., Binding of GAP to Activated PDGF Receptors; Science, 1990, pp. 1578–1581.

Coughlin et al., Role ofd Phosphatidylinositol Kinase in PDGF Receptor Signal Transduction, Science, vol. 243, 1989, pp. 1191–1194.

Morrison et al., Signal transduction from membrane to cytoplasm: Growth factors and membrane–bound oncogene products increase Raf–1 phosphorylation and associated protein kinase activity; Proc. Natl. Acad. Asc. USA, vol. 89, pp. 8855–8859, 1988 Biochemistry.

Molloy et al., PDGF induction of tyrosine phosphorylation of GTPase activating protein, Letters to Nature, vol. 342, pp. 711–714, 1989.

Varticovski et al., The colony stimulating factor–1 receptor associates with and activates phosphatidylinositol–3 kinase, Letters to Nature, vol. 342, pp. 699–702, 1989.

Fazioli et al., The erbB–2 Mitogenic Signaling Pathway: Tyrosine Phosphorylation of Phospholipase C–y and GTPase–Activating Protein Does Not Correlated with erbB–2 Mitogenic Potency, Moleculat and Cellular Biology, 1991, pp./ 2040–2048.

Segatto et al., The Juxtamembrane Regions of the Epiderma 1 Growth Factor Receptor and $gp185^{erbB-2}$ Determine the Specificity of Signal Transduction, Molecular and Cellular Biology, 1991, pp. 3191–3202.

Gould et al., Platelet–Derived Growth Factor Induces Multisite Phosphorylation of $pp60^{c-src}$ and Increases Its Protein–Tyrosine Kinase Activity, Molecular and Cellular Biology, 1988, pp. 3345–3356.

Wahl et al., Platelet–Derived Growth Factor Induces Rapid and Sustained Tyrosine Phosphorylation of Phospholipase C–y in Quiescent BALB/c 3T3 Cells, Molecular and Cellular Biology, 1989, pp. 2934–3943.

Avivi et al., Comparison of EFT receptor sequences as a guide to study the ligand binding site, Oncogene (1991), 6, pp. 673–676.

Rusch et al., The Epidermal Growth Factor Receptor and Its Ligands as Therapeutic Targets in Human Tumors, Cytokine & Growth Factor Review, vol. 2, No. 2, pp. 133–141–1996 —pp. 133–141.

Cohen, Epidermal Growth Factor, Bioscience Reports, vol. 6, No. 12, 1986—pp. 1017–1028.

Modjtahedi et al., Antitumor Activity of Combinations of Antibodies Directed Against Different Epitopes on the Extracellular Domain of the Human EGF Receptor, Cell Biophysics, vol. 22, 1993—pp. 129–146.

Buolamwini—Novel anticancer drug discover—pp. 500–509.

Dean et al., Immunotherapy with Antibodies to the EGF Receptor, Int. J. Cancer: Supplement 8, 1994—pp. 103–107.

Scher et al., Changing Pattern of Expression of the Epidermal Growth Factor Receptor and Transforming Growth Factor a in the Progression of Prostatic Neoplasms, Clinical Cancer Res., vol. 1, 1995—pp. 545–550.

Kita et al., ErbB Receptor Activation, Cell Morphology Changes, and Apoptosis Induced by Anti–Her2 Monoclonal Antibodies, Biochemical and Biophysical Research Comm., vol. 222, 1996, pp. 59–69.

Funding cancer research—Editorial—Nature Medicine, vol. 4, No. 3. 1998.

Normanno et al., Growth Inhibition of Human Colon Carcinoma Cells by Combinations of Anti–Epidermal Growth Factor–related Growth Factor Antisense Oligonucleotides, Clinical Cancer Research, vol. 2, 1996, pp. 601–609.

Favoni et al., The Role of Polypeptide Growth Factors in Human Carcinomas: New Targets for a Novel Pharmacological Approach, Pharmacological Reviews, vol. 52, No. 2, pp. 179–206.

Grandis et al., Asynchronous Modulation of Transforming Growth Factor a and Epidermal Growth Factor Receptor Protein Expression in Progression of Premalignant Lesions to Head and Neck Squamous Cell Carcinoma, Clinical Cancer Research, vol. 4, 1998, pp. 13–20.

Nass et al., Epidermal Growth Factor–dependent Cell Cycle Progression is Altered in mammary Epithelial Cells that overexpress c–myc. Clinical Cancer Research, vol. 4, 1998, pp. 1813–1822.

Friess et al., Molecular Aspects of Pancreatic Cancer and Future Perspectives, Dig. Surg. vol. 16, 1999, pp. 281–290.

Tecce et al., Characterization of Cytotoxic Activity of Saporin Anti–GP 185/HER–2 Immunotoxins, Int. J. Cancer, vol. 55, 1993, pp. 122–127.

Nicholson et al., Epidermal growth factor receptor (EGFr); results of a 76 year follow–up study in operable breast cancer with emphasis on the node negative subgroup, Br. J. Cancer, vol. 63, 1991, pp. 146–150.

Kirk et al., Selective toxicity of TGF–1PE40 to EGFR–positive cell lines: selective protection of low EGFR–expressing cell lines by EGF, Br. J. Cancer, vol. 69, 1994, pp. 988–994.

Harris et al., Epidermal Growth Factor Receptor and Other Oncogenes as Prognostic Markers, J. Nat. Cancer Institute Monographs, No. 11, pp. 181–187.

Witters et al., Antisense oligonucleotides to the epidermal growth factor receptor. Breast Cancer Research and Treatment, vol. 53, 1999, pp. 41–50.

Derynck et al., Synthesis of Messenger RNAs for Transforming Growth Factors a and B and the Epidermal Growth Factor Receptor by Human Tumors, Cancer Research, vol. 47, 1987, pp. 707–712.

Scher et al., Use of Adaptive Control with Feedback to Individualize Suramin Dosing, Cancer Research, vol. 52, 1992, pp. 64–70.

Fontanini et al., Epidermal Growth Factor Receptor (EGFr) Expression in Non–small Cell Lung Carcinomas Correlates with Metastatic Involvement of Hilar and Mediastinal Lymph Nodes in the Squamous Subtype, Eur J. Cancer, vol. 31A, No. 2, 1995, pp. 178–183.

Eisenberger et al., Suramin, New Drugs, Cancer Treatment Reviews, vol. 20, 1994, pp. 259–273.

Baselga et al., Antitumor Effects of Doxorubicin in Combination With Anti–epidermal Growth Factor Receptor Monoclonal Antibodies, Journal of the National Cancer Institute, vol. 85, No. 16, 1993, pp. 1327–1333.

Divgi et al., Phase I and Imaging Trial and Indium 111–Labeled Anti–Epidermal Growth Factor Receptor Monoclonal Antibody 225 in Patients with Squamous Cell Lung Carcinoma, Journal of the National Cancer Institute, vol. 83, No. 2, 1991, pp. 97–104.

Fry et al., A Specific Inhibitor of the Epidermal Growth Factor Receptor Tyrosine Kinase, Science, vol. 265, 1994, pp. 1093–1095.

Perez–Soler et al., Tumor Epidermal Growth Factor Receptor Studies in Patients with Non–Small–Cell Lung Caner or Head and Neck Cancer Treated with Monoclonal Antibody RG 83852, Journal of Clinical Oncology, vol. 12, No. 4, 1994, pp. 730–739.

Pregram et al., Phase II Study of Receptor–Enhanced Chemosensitivity Using Recombinant Humanized Anti–p 185HER2/neu Monoclonal Antibody Plus Cisplatin in Patients with HER2/neu–Overexpressing Metastatic Breast Cancer Refractory to Chemitherapy Treatment, Journal of Clinical Oncology, vol. 16, No. 8, 1998, pp. 2659–2671.

Fan et al., Antitumor Effect of Anti–Epidermal Growth Factor Receptor Monoclonal Antibodies plus cis–Diamminedichloroplatinum on Well Established A431 Cell Xenografts, Cancer Research, vol. 53, 1993, pp. 4637–4642.

* cited by examiner

```
  1   GGGTGTTTTA TTTCCTCCTC TTCTTCCCGC ACTGTGCGCT CCTCCTGGGC TAGGGCGTCT

61   GGATCGAGTC CCGGAGGCTA CCGCCTCCCA GACAGACGAC GGGTCACCTG GACGCGAGCC

121   TGTGTCCGGG TCTCGTCGTT GCCGGCGCAG TCACTGGGCA CAACCGTGGG ACTCCGTCTG

181   TCTCGGATTA ATCCCGGAGA GCCAGAGCCA ACCTCTCCCG GTCAGAGATG CGACCCTCAG
  1                                                        Met ArgProSerG

241   GGACCGCGAG AACCACACTG CTGGTGCTGC TGACCGCGCT CTGCGCGGCA GGTGGGGCGT
  5   lyThrAlaAr gThrThrLeu LeuValLeuL euThrAlaLe uCysAlaAla GlyGlyAlaL

301   TGGAGGAAAA GAAAGTCTGC CAAGGCACAA GTAACAGGCT CACCCAACTG GGCACTTTTG
 25   euGluGluLy sLysValCys GlnGlyThrS erAsnArgLe uThrGlnLeu GlyThrPheG

361   AAGACCACTT TCTGAGCCTG CAGAGGATGT ACAACAACTG TGAAGTGGTC CTTGGGAACT
 45   luAspHisPh eLeuSerLeu GlnArgMetT yrAsnAsnCy sGluValVal LeuGlyAsnL

421   TGGAAATTAC CTATGTGCAA AGGAATTACG ACCTTTCCTT CTTAAAAACC ATCCAGGAGG
 65   euGluIleTh rTyrValGln ArgAsnTyrA spLeuSerPh eLeuLysThr IleGlnGluV

481   TGGCCGGCTA TTTCCTCATT GCCCTCAACA CCGTGGAGAG AATCCCTTCG GAGGACCTGC
 85   alAlaGlyTy rPheLeuIle AlaLeuAsnT hrValGluAr gIleProSer GluAspLeuG

541   AGATCATCAG GGAAATGCT CTTTATGAAA CACCTATGC CTTAGCCATC CTGTCCAACT
105   lnIleIleAr gGlyAsnAla LeuTyrGluA snThrTyrAl aLeuAlaIle LeuSerAsnT

601   ATGGGACAAA CAGAACTGGG CTTAGGGAAC TGCCCATGCG GAACTTACAG GAAATCCTGA
125   yrGlyThrAs nArgThrGly LeuArgGluL euProMetAr gAsnLeuGln GluIleLeuI

661   TTGGTGCTGT GCGATTCAGC AACAACCCCA TCCTCTGCAA TATGGATACT ATCCAGTGGA
145   leGlyAlaVa lArgPheSer AsnAsnProI leLeuCysAs nMetAspThr IleGlnTrpA

721   GGGACATCGT CCAAAACGTC TTTATGAGCA ACATGTCAAT GGACTTACAG AGCCATCCGA
165   rgAspIleVa lGlnAsnVal PheMetSerA snMetSerMe tAspLeuGln SerHisProS

781   GCAGTTGCCC CAAATGTGAT CCAAGCTGTC CCAATGGAAG CTGCTGGGGA GGAGGAGAGG
185   erSerCysPr oLysCysAsp ProSerCysP roAsnGlySe rCysTrpGly GlyGlyGluG

841   AGAACTGCCA GAAATTGACC AAAATCATCT GTGCCCAGCA ATGTTCCCAT CGCTGTCGTG
205   luAsnCysGl nLysLeuThr LysIleIleC ysAlaGlnGl nCysSerHis ArgCysArgG

901   GCAGGTCCCC CAGTGACTGC TGCCACAACC AATGTGCTGC GGGGTGTACA GGGCCCCAAA
225   lyArgSerPr oSerAspCys CysHisAsnG lnCysAlaAl aGlyCysThr GlyProGlnL
```

FIG. 1(a)

```
 961  AGAGTGACTG TCTGGTCTGC CAAAAGTTCC AAGATGAGGC CACATGCAAA GACACCTGCC
 245  ysSerAspCy sLeuValCys GlnLysPheG lnAspGluAl aThrCysLys AspThrCysP

1021  CACCACTCAT GCTGTACAAC CCCACCACCT ATCAGATGGA TGTCAACCCT GAAGGGAAGT
 265  roProLeuMe tLeuTyrAsn ProThrThrT yrGlnMetAs pValAsnPro GluGlyLysT

1081  ACAGCTTTGG TGCCACCTGT GTGAAGAACT GCCCCCGAAA CTACGTGGTG ACAGATCATG
 285  yrSerPheGl yAlaThrCys ValLysAsnC ysProArgAs nTyrValVal ThrAspHisG

1141  GCTCATGTGT CCGAGCCTGT GGGCCTGACT ACTACGAAGT GGAAGAAGAT GGCATCCGCA
 305  lySerCysVa lArgAlaCys GlyProAspT yrTyrGluVa lGluGluAsp GlyIleArgL

1201  AGTGTAAAAA ATGTGATGGG CCCTGTCGCA AAGTTTGTAA TGGCATAGGC ATTGGTGAAT
 325  ysCysLysLy sCysAspGly ProCysArgL ysValCysAs nGlyIleGly IleGlyGluP

1261  TTAAAGACAC ACTCTCCATA AATCGTACAA ACATCAAACA CTTCAAATAC TGCACTGCCA
 345  heLysAspTh rLeuSerIle AsnAlaThrA snIleLysHi sPheLysTyr CysThrAlaI

1321  TCAGCGGGGA CCTTCACATC CTGCCAGTGG CCTTTAAGGG GGATTCTTTC ACGCGCACTC
 365  leSerGlyAs pLeuHisIle LeuProValA laPheLysGl yAspSerPhe ThrArgThrP

1381  CTCCTCTAGA CCCACGGGAA CTAGAAATTC TCAAGACTGT GAAGGAAATA ACAGGGTCTT
 385  roProLeuAs pProArgGlu LeuGluIleL euLysThrVa lLysGluIle ThrGlySerL

1441  TGCTGATTCA GGCTTGGCCT GAAAACTGGA CTGACCTCCA TGCTTTTGAG AACCTAGAAA
 405  euLeuIleGl nAlaTrpPro GluAsnTrpT hrAspLeuHi sAlaPheGlu AsnLeuGluI

1501  TAATTCGTGG CAGAACAAAG CAACATGGTC AGTTTTCTCT GGCGGTTGTC GGCCTGAACA
 425  leIleArgGl yArgThrLys GlnHisGlyG lnPheSerLe uAlaValVal GlyLeuAsnI

1561  TAACATCGCT GCCGTGGCAG GTTCCATCGC TGTCGTGGCA GGCTGTGACA AGGCCCTTGC
 445  leThrSerLe uProTrpGln ValProSerL euSerTrpGl nAlaValThr ArgProLeuH

1621  ACCCTCTGGC CCAAAATAGA GTCAGCTGGG ACACTGGGCC CTGACCTTGT AAGCTTCCTG
 465  isProLeuAl aGlnAsnArg ValSerTrpA spThrGlyPr o---                 478

1681  TAATGTTAGC CTGCCCATGG CACCCCAACA GCAAGATCCT GAAGCTCAAG TTTGATCCTA

1741  ACAAAACCAC CGCTGCTGCG GTTTCTGGGA GAAGCAAGCA TTTATTCACC TGCAAGATCA

1801  CATCCCTAAC CTTGACTTTG CTTAAGAGTG CTGAATGAAG ATCCTGTCCC TAAATCATAA

1861  CTCAATTCTT TTGCTCAAGG AAAATGCACT TGTCTTCTTC CAAAAAAAAA AAATCAATAT

1921  GCAAAATGGA ATTTGAAATA AAAGCTTTTC TAAAAATG                         1958
```

FIG.1(b)

```
   1  GGGTGTTTTA TTTCCTCCTC TTCTTCCCGC ACTGTGCGCT CCTCCTGGGC TAGGGCGTCT
  61  GGATCGAGTC CCGGAGGCTA CCGCCTCCCA GACAGACGAC GGGTCACCTG GACGCGAGCC
 121  TGTGTCCGGG TCTCGTCGTT GCCGGCGCAG TCACTGGGCA CAACCGTGGG ACTCCGTCTG
 181  TCTCGGATTA ATCCCGGAGA GCCAGAGCCA ACCTCTCCCG GTCAGAGATG CGACCCTCAG
 241  GGACCGCGAG AACCACACTG CTGGTGCTGC TGACCGCGCT CTGCGCGGCA GGTGGGGCGT
 301  TGGAGGAAAA GAAAGTCTGC CAAGGCACAA GTAACAGGCT CACCCAACTG GGCACTTTTG
 361  AAGACCACTT TCTGAGCCTG CAGAGGATGT ACAACAACTG TGAAGTGGTC CTTGGGAACT
 421  TGGAAATTAC CTATGTGCAA AGGAATTACG ACCTTTCCTT CTTAAAAACC ATCCAGGAGG
 481  TGGCCGGCTA TTTCCTCATT GCCCTCAACA CCGTGGAGAG AATCCCTTCG GAGGACCTGC
 541  AGATCATCAG GGGAAATGCT CTTTATGAAA ACACCTATGC CTTAGCCATC CTGTCCAACT
 601  ATGGGACAAA CAGAACTGGG CTTAGGGAAC TGCCCATGCG GAACTTACAG GAAATCCTGA
 661  TTGGTGCTGT GCGATTCAGC AACAACCCCA TCCTCTGCAA TATGGATACT ATCCAGTGGA
 721  GGGACATCGT CCAAAACGTC TTTATGAGCA ACATGTCAAT GGACTTACAG AGCCATCCGA
 781  GCAGTTGCCC CAAATGTGAT CCAAGCTGTC CCAATGGAAG CTGCTGGGGA GGAGGAGAGG
 841  AGAACTGCCA GAAATTGACC AAAATCATCT GTGCCCAGCA ATGTTCCCAT CGCTGTCGTG
 901  GCAGGTCCCC CAGTGACTGC TGCCACAACC AATGTGCTGC GGGGTGTACA GGGCCCCAAA
 961  AGAGTGACTG TCTGGTCTGC CAAAAGTTCC AAGATGAGGC CACATGCAAA GACACCTGCC
1021  CACCACTCAT GCTGTACAAC CCCACCACCT ATCAGATGGA TGTCAACCCT GAAGGGAAGT
1081  ACAGCTTTGG TGCCACCTGT GTGAAGAACT GCCCCCGAAA CTACGTGGTG ACAGATCATG
1141  GCTCATGTGT CCGAGCCTGT GGGCCTGACT ACTACGAAGT GGAAGAAGAT GGCATCCGCA
1201  AGTGTAAAAA ATGTGATGGG CCCTGTCGCA AAGTTTGTAA TGGCATAGGC ATTGGTGAAT
1261  TTAAAGACAC ACTCTCCATA AATGCTACAA ACATCAAACA CTTCAAATAC TGCACTGCCA
1321  TCAGCGGGGA CCTTCACATC CTGCCAGTGG CCTTTAAGGG GGATTCTTTC ACGCGCACTC
1381  CTCCTCTAGA CCCACGGGAA CTAGAAATTC TCAAGACTGT GAAGGAAATA ACAGGGTCTT
1441  TGCTGATTCA GGCTTGGCCT GAAAACTGGA CTGACCTCCA TGCTTTTGAG AACCTAGAAA
1501  TAATTCGTGG CAGAACAAAG CAACATGGTC AGTTTTCTCT GGCGGTTGTC GGCCTGAACA
1561  TAACATCGCT GCCGTGGCAG GTTCCATCGC TGTCGTGGCA GGCTGTGACA AGGCCCTTGC
1621  ACCCTCTGGC CCAAAATAGA GTCAGCTGGG ACACTGGGCC CTGACCTTGT AAGCTTCCTG
1681  TAATGTTAGC CTGCCCATGG CACCCCAACA GCAAGATCCT GAAGCTCAAG TTTGATCCTA
1741  ACAAAACCAC CGCTGCTGCG GTTTCTGGGA GAAGCAAGCA TTTATTCACC TGCAAGATCA
1801  CATCCCTAAC CTTGACTTTG CTTAAGAGTG CTGAATGAAG ATCCTGTCCC TAAATCATAA
1861  CTCAATTCTT TTGCTCAAGG AAAATGCACT TGTCTTCTTC CAAAAAAAAA AAATCAATAT
1921  GCAAAATGGA ATTTGAAATA AAAGCTTTTC TAAAAATG Poly-A
```

FIG.2

```
MRPSGTARTTLLVLLTALCAAGGALEEKKVCQGTSNRLTQLGTFEDHFLSLQRMYNNCEVVLGNLEITYVQRNYDLSFL
KTIQEVAGYFLIALNTVERIPSEDLQIIRGNALYENTYALAILSNYGTNRTGLRELPMRNLQEILIGAVRFSNNPILCN
MDTIQWRDIVQNVFMSNMSMDLQSHPSSCPKCDPSCPNGSCWGGGEENCQKLTKIICAQQCSHRCRGRSPSDECHNQCA
AGCTGPQKSDCLVCQKFQDEATCKDTCPPLMLYNPTTYQMDVNPEGKYSFGATCVKNCPRNYVVTDHGSCVRACGPDYY
EVEEDGIRKCKKCDGPCRKVCNGIGIGEFKDTLSINATNIKHFKYCTAISGDLHILPVAFKGDSFTRTPPLDPRELEIL
KTVKEITGSLLIQAWPENWTDLHAFENLEIIRGRTKQHGQFSLAVVGLNITSLPWQVPSLSWQAVTRPLHPLAQNRVSW
DTGP*
```

FIG.3

FIG. 4 SCHEMATIC MAP OF RAT ERRP cDNA

FIG. 9 CLONOGENIC ASSAY

FIG.13 TUMOR GROWTH IN SCID MICE XENOGRAFTS

SEQUENCE LISTING

<160> NUMBER OF SEQ ID NOS: 8

<210> SEQ ID NO 1
<211> LENGTH: 1958
<212> TYPE: DNA
<213> ORGANISM: Rattus norvegicus

<400> SEQUENCE: 1

| | | | | | |
|---|---|---|---|---|---|
| gggtgtttta | tttcctcctc | ttcttcccgc | actgtgcgct | cctcctgggc | tagggcgtct | 60 |
| ggatcgagtc | ccggaggcta | ccgcctccca | gacagacgac | gggtcacctg | gacgcgagcc | 120 |
| tgtgtccggg | tctcgtcgtt | gccggcgcag | tcactgggca | caaccgtggg | actccgtctg | 180 |
| tctcggatta | atcccggaga | gccagagcca | acctctcccg | gtcagagatg | cgaccctcag | 240 |
| ggaccgcgag | aaccacactg | ctggtgctgc | tgaccgcgct | ctgcgcggca | ggtggggcgt | 300 |
| tggaggaaaa | gaaagtctgc | caaggcacaa | gtaacaggct | cacccaactg | ggcacttttg | 360 |
| aagaccactt | tctgagcctg | cagaggatgt | acaacaactg | tgaagtggtc | cttgggaact | 420 |
| tggaaattac | ctatgtgcaa | aggaattacg | acctttcctt | cttaaaaacc | atccaggagg | 480 |
| tggccggcta | tttcctcatt | gccctcaaca | ccgtggagag | aatcccttcg | gaggacctgc | 540 |
| agatcatcag | gggaaatgct | ctttatgaaa | acacctatgc | cttagccatc | ctgtccaact | 600 |
| atgggacaaa | cagaactggg | cttagggaac | tgcccatgcg | gaacttacag | gaaatcctga | 660 |
| ttggtgctgt | gcgattcagc | aacaacccca | tcctctgcaa | tatggatact | atccagtgga | 720 |
| gggacatcgt | ccaaaacgtc | tttatgagca | acatgtcaat | ggacttacag | agccatccga | 780 |
| gcagttgccc | caaatgtgat | ccaagctgtc | ccaatggaag | ctgctgggga | ggaggagagg | 840 |
| agaactgcca | gaaattgacc | aaaatcatct | gtgcccagca | atgttcccat | cgctgtcgtg | 900 |
| gcaggtcccc | cagtgactgc | tgccacaacc | aatgtgctgc | ggggtgtaca | gggcccccaaa | 960 |
| agagtgactg | tctggtctgc | caaaagttcc | aagatgaggc | cacatgcaaa | gacacctgcc | 1020 |
| caccactcat | gctgtacaac | cccaccacct | atcagatgga | tgtcaaccct | gaagggaagt | 1080 |
| acagctttgg | tgccacctgt | gtgaagaact | gcccccgaaa | ctacgtggtg | acagatcatg | 1140 |
| gctcatgtgt | ccgagcctgt | gggcctgact | actacgaagt | ggaagaagat | ggcatccgca | 1200 |
| agtgtaaaaa | atgtgatggg | ccctgtcgca | agtttgtaa | tggcataggc | attggtgaat | 1260 |
| ttaaagacac | actctccata | aatgctacaa | acatcaaaca | cttcaaatac | tgcactgcca | 1320 |
| tcagcgggga | ccttcacatc | ctgccagtgg | cctttaaggg | ggattctttc | acgcgcactc | 1380 |
| ctcctctaga | cccacgggaa | ctagaaattc | tcaagactgt | gaaggaaata | acagggtctt | 1440 |
| tgctgattca | ggcttggcct | gaaaactgga | ctgacctcca | tgctttttgag | aacctagaaa | 1500 |
| taattcgtgg | cagaacaaag | caacatggtc | agttttctct | ggcggttgtc | ggcctgaaca | 1560 |

-continued

```
taacatcgct gccgtggcag gttccatcgc tgtcgtggca ggctgtgaca aggcccttgc   1620
accctctggc ccaaaataga gtcagctggg acactgggcc ctgaccttgt aagcttcctg   1680
taatgttagc ctgcccatgg cacccccaaca gcaagatcct gaagctcaag tttgatccta   1740
acaaaaccac cgctgctgcg gtttctggga gaagcaagca tttattcacc tgcaagatca   1800
catccctaac cttgactttg cttaagagtg ctgaatgaag atcctgtccc taaatcataa   1860
ctcaattctt ttgctcaagg aaaatgcact tgtcttcttc caaaaaaaaa aaatcaatat   1920
gcaaaatgga atttgaaata aaagcttttc taaaaatg                           1958
```

<210> SEQ ID NO 2
<211> LENGTH: 478
<212> TYPE: PRT
<213> ORGANISM: Rattus norvegicus

<400> SEQUENCE: 2

```
Met Arg Pro Ser Gly Thr Ala Arg Thr Thr Leu Leu Val Leu Leu Thr
 1               5                  10                  15

Ala Leu Cys Ala Ala Gly Gly Ala Leu Glu Glu Lys Lys Val Cys Gln
                20                  25                  30

Gly Thr Ser Asn Arg Leu Thr Gln Leu Gly Thr Phe Glu Asp His Phe
            35                  40                  45

Leu Ser Leu Gln Arg Met Tyr Asn Asn Cys Glu Val Val Leu Gly Asn
        50                  55                  60

Leu Glu Ile Thr Tyr Val Gln Arg Asn Tyr Asp Leu Ser Phe Leu Lys
    65                  70                  75                  80

Thr Ile Gln Glu Val Ala Gly Tyr Phe Leu Ile Ala Leu Asn Thr Val
                85                  90                  95

Glu Arg Ile Pro Ser Glu Asp Leu Gln Ile Ile Arg Gly Asn Ala Leu
               100                 105                 110

Tyr Glu Asn Thr Tyr Ala Leu Ala Ile Leu Ser Asn Tyr Gly Thr Asn
           115                 120                 125

Arg Thr Gly Leu Arg Glu Leu Pro Met Arg Asn Leu Gln Glu Ile Leu
       130                 135                 140

Ile Gly Ala Val Arg Phe Ser Asn Asn Pro Ile Leu Cys Asn Met Asp
145                 150                 155                 160

Thr Ile Gln Trp Arg Asp Ile Val Gln Asn Val Phe Met Ser Asn Met
               165                 170                 175

Ser Met Asp Leu Gln Ser His Pro Ser Ser Cys Pro Lys Cys Asp Pro
           180                 185                 190

Ser Cys Pro Asn Gly Ser Cys Trp Gly Gly Glu Glu Asn Cys Gln
       195                 200                 205

Lys Leu Thr Lys Ile Ile Cys Ala Gln Gln Cys Ser His Arg Cys Arg
       210                 215                 220

Gly Arg Ser Pro Ser Asp Cys Cys His Asn Gln Cys Ala Ala Gly Cys
225                 230                 235                 240

Thr Gly Pro Gln Lys Ser Asp Cys Leu Val Cys Gln Lys Phe Gln Asp
               245                 250                 255

Glu Ala Thr Cys Lys Asp Thr Cys Pro Pro Leu Met Leu Tyr Asn Pro
           260                 265                 270

Thr Thr Tyr Gln Met Asp Val Asn Pro Glu Gly Lys Tyr Ser Phe Gly
       275                 280                 285

Ala Thr Cys Val Lys Asn Cys Pro Arg Asn Tyr Val Val Thr Asp His
   290                 295                 300
```

```
Gly Ser Cys Val Arg Ala Cys Gly Pro Asp Tyr Tyr Glu Val Glu
305                 310                 315                 320

Asp Gly Ile Arg Lys Cys Lys Lys Cys Asp Gly Pro Cys Arg Lys Val
                325                 330                 335

Cys Asn Gly Ile Gly Ile Gly Glu Phe Lys Asp Thr Leu Ser Ile Asn
                340                 345                 350

Ala Thr Asn Ile Lys His Phe Lys Tyr Cys Thr Ala Ile Ser Gly Asp
                355                 360                 365

Leu His Ile Leu Pro Val Ala Phe Lys Gly Asp Ser Phe Thr Arg Thr
                370                 375                 380

Pro Pro Leu Asp Pro Arg Glu Leu Glu Ile Leu Lys Thr Val Lys Glu
385                 390                 395                 400

Ile Thr Gly Ser Leu Leu Ile Gln Ala Trp Pro Glu Asn Trp Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Gly Leu Asn Ile Thr Ser Leu
                435                 440                 445

Pro Trp Gln Val Pro Ser Leu Ser Trp Gln Ala Val Thr Arg Pro Leu
                450                 455                 460

His Pro Leu Ala Gln Asn Arg Val Ser Trp Asp Thr Gly Pro
465                 470                 475

<210> SEQ ID NO 3
<211> LENGTH: 35
<212> TYPE: DNA
<213> ORGANISM: Rattus norvegicus
<220> FEATURE:
<223> OTHER INFORMATION: Reverse primer for RACE

<400> SEQUENCE: 3
gactcgagtc gacatcgatt tttttttttt ttttt                              35

<210> SEQ ID NO 4
<211> LENGTH: 22
<212> TYPE: DNA
<213> ORGANISM: Rattus norvegicus
<220> FEATURE:
<223> OTHER INFORMATION: Forward primer for RACE

<400> SEQUENCE: 4
cgcactcctc ctctagaccc ac                                            22

<210> SEQ ID NO 5
<211> LENGTH: 22
<212> TYPE: DNA
<213> ORGANISM: Rattus norvegicus
<220> FEATURE:
<223> OTHER INFORMATION: Forward primer B  for ERRP

<400> SEQUENCE: 5
cgcactcctc ctctagaccc ac                                            22

<210> SEQ ID NO 6
<211> LENGTH: 20
<212> TYPE: DNA
<213> ORGANISM: Rattus norvegicus
<220> FEATURE:
<223> OTHER INFORMATION: Reverse primer T3 for ERRP

<400> SEQUENCE: 6
```

-continued

```
attaaccctc actaaaggga                                                    20

<210> SEQ ID NO 7
<211> LENGTH: 20
<212> TYPE: DNA
<213> ORGANISM: Rattus norvegicus
<220> FEATURE:
<223> OTHER INFORMATION: GAPDH forward pimer

<400> SEQUENCE: 7
accacagtcc atgccatcac                                                    20

<210> SEQ ID NO 8
<211> LENGTH: 20
<212> TYPE: DNA
<213> ORGANISM: Rattus norvegicus
<220> FEATURE:
<223> OTHER INFORMATION: GAPDH reverse primer

<400> SEQUENCE: 8
tccaccaccc tgttgctgta                                                    20
```

RECOMBINANT DNA ENCODING AN EPIDERMAL GROWTH FACTOR RECEPTOR RELATED PROTEIN

This is a divisional application of U.S. patent application Ser. No. 09/570,454, which was filed on May 12, 2000, now issued as U.S. Pat. No. 6,399,743, and which is incorporated herein by reference.

This work has been supported by the Department of Veterans Affairs. The United States Government retains certain rights in this invention.

FIELD OF THE INVENTION

This invention relates to the epidermal growth factor related proteins, polynucleotides encoding these proteins and methods for using these proteins. The cellular machinery involved in mitogenesis is complex, and not yet fully understood. In general, receptors present on the cell surface bind growth factors, resulting in an activated receptor. In particular, tyrosine kinase receptors (TKRs) are endowed with intrinsic tyrosine kinase activity. The activated receptors, in turn, phosphorylate intracellular substrates. These phosphorylated substrates are responsible for a series of events that leads to cell division. This process is generally referred to as "mitogenic signal transduction." The molecular machinery involved in this process is considered to be the "mitogenic signaling pathway."

Growth factors and hormones exert pleiotropic effects on cellular functions, including mitogenic stimulation and modulation of differentiation and metabolism (Ullrich, et al. Cell 61:203–212 (1990); Aaronson, S. A. Science 254: 1146–1153 (1991)). In many cases, these actions are mediated by the interaction of growth factors with cell surface tyrosine kinase receptors (TKRs), which results in enhanced receptor catalytic activity and tyrosine phosphorylation of intracellular substrates (Ullrich, et al., supra, Aaronson, supra). Knowledge of the nature of these second messenger systems is still scanty, although some molecules which associate and/or are tyrosine phosphorylated by TKRs have been identified. These include the γ isozyme of phospholipase C (PLC-7) (Margolis, et al. Call 57: 1101–1107 (1989), Meinsenhelder, et al. Cell 57: 1109–1122 (1989) and Wahl, et al. Mol. Cell. Biol. 9: 2934–2943 (1989)); the p21ras GTPase activating protein (GAP) (Molloy, et al. Nature 342: 711–714 (1989), Kaplan, et al. Cell 61:125–133 (1990), and Kazlauskas, et al. Science 247: 1578–1581 (1990)); the raf serine-threonine kinase (Morrison, et al. Proc. Natl. Acad. Sci. USA 85: 8855–8859 (1988), and Morrison, et al. Cell 58: 649–657 (1989)); the p85 subunit of the phosphatidylinositol 3-kinase (Ptdlns-3K); (Coughlin, et al. Science 243: 1191–1194 (1989) Kazlauskas, et al. Cell 58: 1121–1133 (1989), Varticovski, et al. Nature 342: 699–702 (1989), Ruderman, et al. Proc. Natl. Acad. Sci. USA 87: 1411–1415 (1990), Escobedo, et al. Cell 65: 75–82 (1991), Skolnik, et al. Cell 65: 83–90 (1991), Otsu, et al. Cell 65: 91–104 (1991)) and some cytoplasmic tyrosine kinases (Gould, et al. Mol. Cell. Biol. 8: 3345–3356 (1988); Kypta, et al. Cell 62: 481–492 (1990)). These signaling molecules are thought to mediate at least in part the mitogenic effects of TKRs (Ullrich, et al. supra; Aaronson, supra).

However, the Epidermal growth factor (EGF) receptor (EGFR) does not appear to efficiently interact with known second messenger systems (Fazioli, et al. Mol. Cell. Biol. 11: 2040–2048 (1991); Segatto, et al. Mol. Cell. Biol. 11: 3191–3202 (1991)). Thus, there is need to ascertain the mechanism by which the EGFR functions in mitogenesis, and a particular need to identify and characterize the substrate (if any) of the EGFR.

Errors which occur in the mitogenic signaling pathway, such as alterations in one or more elements of that pathway, are implicated in malignant transformation and cancer. It is believed that in at least some malignancies, interference with such abnormal mitogenic signal transduction could cause the cells to revert to normal phenotype.

In addition, reagents useful in identifying molecular components of the mitogenic signaling pathway find utility as tumor markers for therapeutic, diagnostic, and prognostic purposes. Furthermore, identification of how such components differ from normal components in malignant tissue would be of significant value in understanding and treating such malignancies.

EGFR, a 170 kDa transmembrane glycoprotein protein with intrinsic tyrosine kinase activity, which binds EGF family of peptides, plays an important role in controlling cell proliferation and differentiation as was shown by Ullrich et al. supra. The EGFR possesses three functional domains that include extracellular, transmembrane and cytoplasmic. Ligand binding to the extacellular domain of EGFR leads to dimerization and activation of the receptor's intrinsic tyrosine kinase, located in the cytoplasmic domain, triggering a complex array of enzymatic and biological events leading to cell proliferation and differentiation.

Overexpression of EGFR has been associated with many malignancies, including cancers of the stomach and colon. Evidence is accumulating which show that malignant as well as certain normal cells also produce other form(s) of EGFR. For example, A431 human epidermoid carcinoma cells have been shown to produce a truncated EGFR that encodes a 2.8 kb mRNA transcript and is thought to be the result of gene rearrangement in chromosome 7. Likewise, the normal rat liver produces a 2.7 kb mRNA transcript whose 5', but not 3', sequences show 100% homology with the external domain of the full-length rat EGFR. This and other relevant observations suggest that this truncated form of EGFR mRNA, whose protein product is also secreted from the cell, is generated from alternative splicing of the primary EGFR transcript. A shorter 1.8 kb alternative transcript from the human EGFR, which also produces a secreted product, has been isolated from a human placental cDNA library (Reiter J. L., Maihle, N. J. Nucleic Acid Research 24:4050–4056, 1996).

SUMMARY OF THE INVENTION

The present invention is directed toward a polynucleotide sequence, proteins transcribed from the nucleotide sequence, methods for the use of epidermal growth factor receptor related protein (ERRP) as well as probes for the detection of m-RNA, DNA and cDNA of the described nucleotide sequence and monoclonal antibodies directed toward ERRP.

In particular, a cDNA fragment clone of 1583 base pairs with 90–95% sequence homology to mouse epidermal growth factor receptor (EGFR) and a truncated rat EGFR was isolated. The full length cDNA revealed 1958 base pairs (SEQ ID NO: 1) that contained 227 base pairs of 5' untranslated region and an open reading frame encoding 478 amino acids (SEQ. ID NO: 2) followed by 290 base pairs of an untranslated region. The full length cDNA showed an 84% and 91% homology, respectively, to a rat truncated EGFR and the mouse EGFR. The product of the newly isolated DNA is referred to as ERRP (EGF-Receptor Related Protein). In a Northern-blot analysis with poly A⁺ RNA from different rate tissues, ERRP cDNA hybridized strongly to a mRNA transcript of about 1.8 Kb. Maximal expression was noted in the small intestine, followed by colon, liver gastric mucosa and other tissue. Transfection of ERRP cDNA in HCT-116 cells, a colon cancer cell line, markedly inhibited (40–60%) proliferation in monolayer and soft agar and also attenuated EGFR tyrosine kinase activity compared to vector-transfected control cells. Proliferation of the vector-transfected control, but not ERRP transfected HCT cells could be stimulated by TGF-α ($10^{-10}$M and $10^{-9}$M). The over expression of ERRP in HCT-116 cell delayed tumor growth in SCID mice xenografts. The ERRP cDNA represents a new member of the EGFR gene family and the protein product plays a key role in modulating the function of EGFR.

BRIEF DESCRIPTION OF THE DRAWINGS

FIGS. 1(a), 1(b): Description of the aligned nucleotide and amino acid sequence of ERRP. (SEQ. ID No: 1 and SEQ. ID NO: 2)

FIG. 2: Description of the nucleotide sequence of ERRP. (SEQ. ID NO: 1)

FIG. 3: Description of the amino acid sequence of ERRP. (SEQ. ID NO: 2)

DETAILED DESCRIPTION OF THE INVENTION

It has been demonstrated that stimulation of gastric mucosal proliferative activity, whether the result of aging, injury or the administration of gastrin, bombesin or EGF to young adult rats, is associated with a rise in tyrosine phosphorylation of a membrane protein with a molecular mass of 55 kDa. A similar phenomenon has also been observed in the colonic mucosa of rats after administration of either gastrin or the colonic carcinogen azoxymethane. These and other relevant observations led us to suggest that the 55 kDa phosphotyrosine mucosal membrane protein, which we have referred to as pp55, may play a role in modulating gastrointestinal mucosal cell proliferation.

During the course of screening the cDNA expression library with pp55 antibodies, we isolated a cDNA fragment clone of 1583 base pairs (bp) which showed a 95% sequence homology to the extracellular domain of the mouse EGFR and an 92% homology to a truncated rat EGFR. We refer to the product of this clone as ERRP (EGRR Related Protein). The 1583 bp cDNA fragment possessed the "initiation" ATG codon, but lacked the termination codon. In view of this, RACE was applied to obtain the 3'-terminal end, which resulted in a 375 bp fragment with TGA "termination" codon and the 3' poly A tail. The full-length cDNA thus obtained consisted of 1958 bp (SEQ. ID NO: 1) which contained 227 bp 5' untranslated region and an open reading frame (ORF) that coded for 478 amino acids (SEQ. ID NO: 2) which showed a 84% and 91% homology, respectively, with the rat truncated EGFR and the external domain.

During the course of screening the cDNA expression library with pp55 antibodies, we isolated a cDNA fragment clone of 1583 base pairs (bp) which showed a 95% sequence homology to the extracellular domain of the mouse EGFR and an 92% homology to a truncated rat EGFR. We refer to the product of this clone as ERRP (EGRR Related Protein). The 1583 bp cDNA fragment possessed the "initiation" ATG codon, but lacked the termination codon. In view of this, RACE was applied to obtain the 3'-terminal end, which resulted in a 375 bp fragment with TGA "termination" codon and the 3' poly A tail. The full-length cDNA thus obtained consisted of 1958 bp which contained 227 bp 5' untranslated region and an open reading frame (ORF) that coded for 479 amino acids which showed a 84% and 91% homology, respectively, with the rat truncated EGFR and the external domain of the mouse EGFR. It also possessed a little over 80% homology with the external domain of the human EGFR. However, the first 24 amino acids of the ORF were similar but not identical to those found in the signal peptide of human EGFR. Additionally, a region of the 3' end (referred to as U; nucleotides 1580–1661) encoding 27 amino acids showed no homology with any known sequence in the current data base. The results suggest that ERRP is a new member of the EGFR family.

Figure 4:
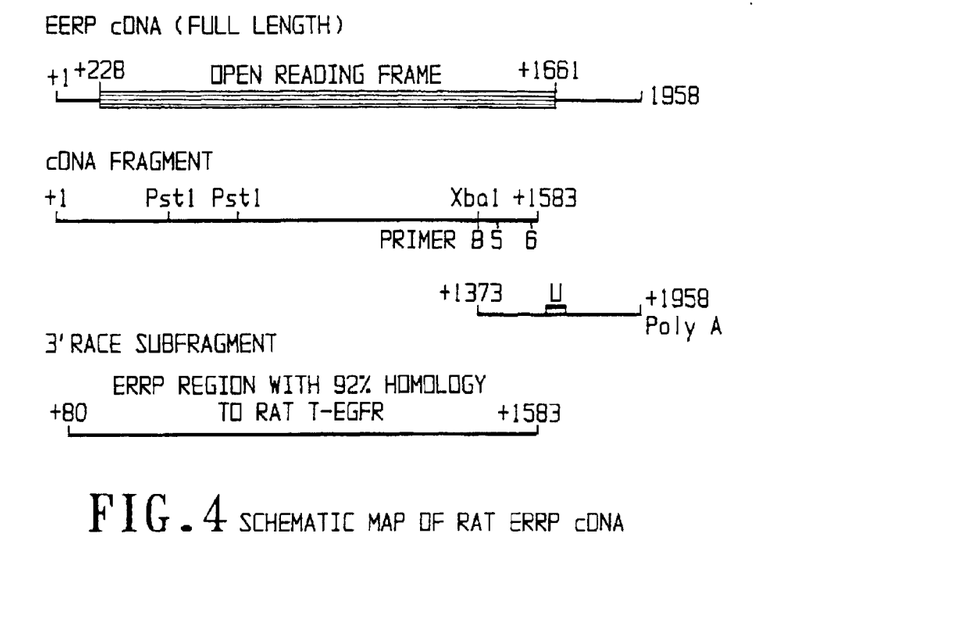
FIG. 4: Schematic representation of ERRP cDNA showing its homology to a rat truncated EGF-R (T-EGER).

The full-length cDNA was isolated and consists of 1958 base pairs (bp) (SEQ. ID NO: 1) that included 227 bp 5' untranslated region (UTR) and a putative open reading frame (ORF) of 1437 nucleotides encoding 479 amino acids, and a 290 nucleotide 3' UTR as is shown in FIG. 4.

Figure 5:
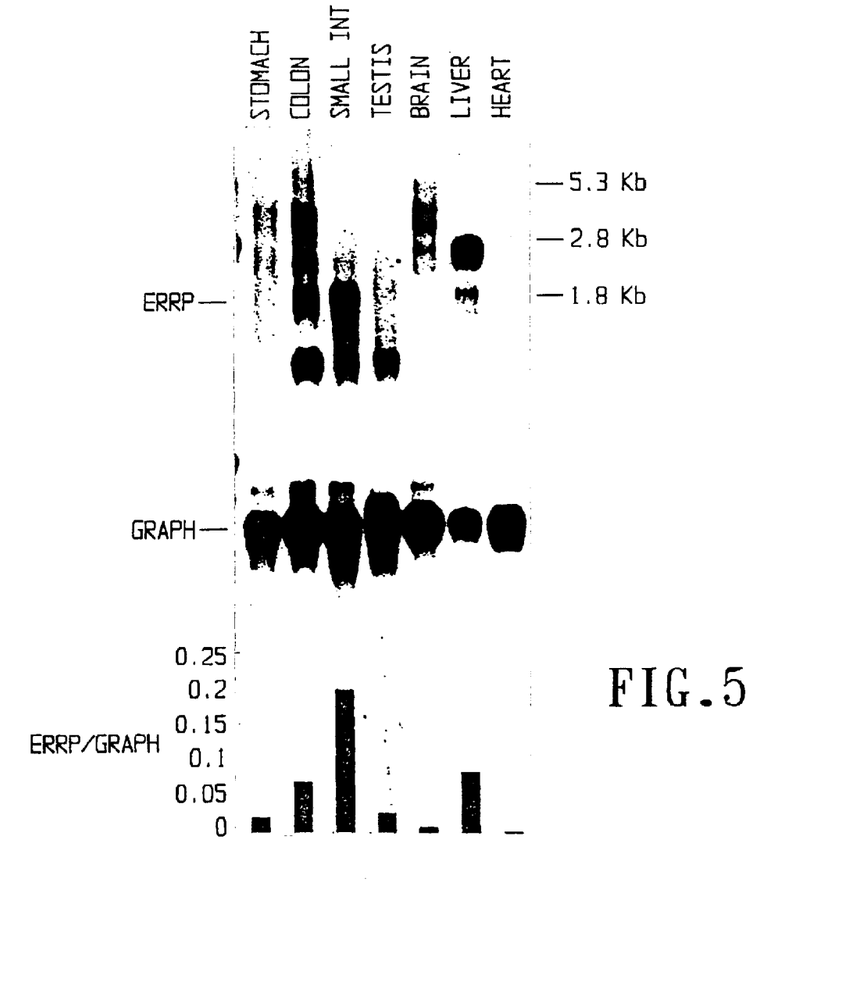
FIG. 5: Northern-blot analysis showing the mRNA transcript size of ERRP in different tissues in rats. Each lane contains 1 µg poly A+ RNA. The membrane was also probed with GAPDH. Changes in relative concentration of ERRP mRNA, expressed as ratio of ERRP to GAPDH, are shown at the bottom of the figure.

To determine the expression of ERRP, Northern-blot analysis was performed with poly A+ RNA from different tissues of the gastrointestinal tract as well as from the liver, brain, heart and testes. Expression of ERRP mRNA varied considerably between the tissues as is shown in FIG. 5. ERRP cDNA hybridized strongly to a mRNA transcript of about 1.8 kb with maximal expression noted in the small intestine, followed by colon, liver, gastric mucosa and other tissues. No hybridization of ERRP cDNA to 1.8 kb mRNA transcript was observed in testes, brain and heart. In addition to the 1.8 kb mRNA transcript, ERRP cDNA also reacted strongly with 2.8 kb transcript in the liver, and with 0.6, 2.8 and 5.0 kb mRNAs in certain tissues, most notably in the colon. The transcript size 5.0 kb may represent EGFR. However, no expression of ERRP mRNA was observed in the heart as is shown in FIG. 5.

Figure 6:
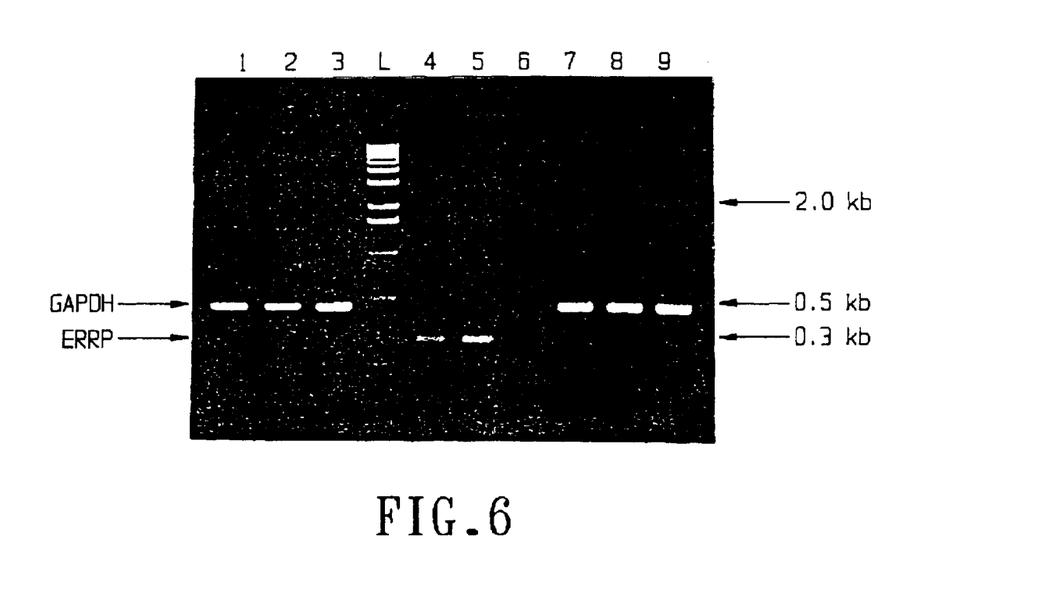
FIG. 6: RT-PCR reaction showing changes in mRNA levels of ERRP and GAPDH in the control (vector-transfected) and ERRP cDNA transfected (clones 1 and 2) HCT-116 cells. RT-PCR was performed with primers for ERRP and GAPDH simultaneously (lanes 1–3) or with primers for ERRP (lanes 4–6) or GAPDH (lanes 7–9). Lanes 1, 2 and 3 represent clones 2, 1 and controls respectively. Lanes 4, 5 and 6 represent clones 2, 1 and control. Lanes 7, 8 and 9 represent clones 2, 1 and controls. Lane L represents DNA ladder.

To determine putative functional properties of ERRP, cDNA for ERRP was stably transfected in HCT-116 cells, a colon cancer cell line. Four ERRP-positive clones, as evidenced by Northern-blot analysis with polyA+ RNA, were selected. For further verification of ERRP transfection, RNA extracted from cells grown from these clones were subsequently subjected to RT-PCR analysis with primers generated from 1.6 kb fragment of the full-length 1.95 kb ERRP. RT-PCR analysis revealed ERRP mRNA in clones #1 and #2 with minimal to no-detectable levels in the other two clones as is shown in FIG. 6. ERRP expression was higher in clone #1 than clone #2. No ERRP mRNA ws detected in control cells (transfected with the vector alone). In contrast, no apparent difference in GAPDH mRNA levels were found among the different clones.

Figure 7:
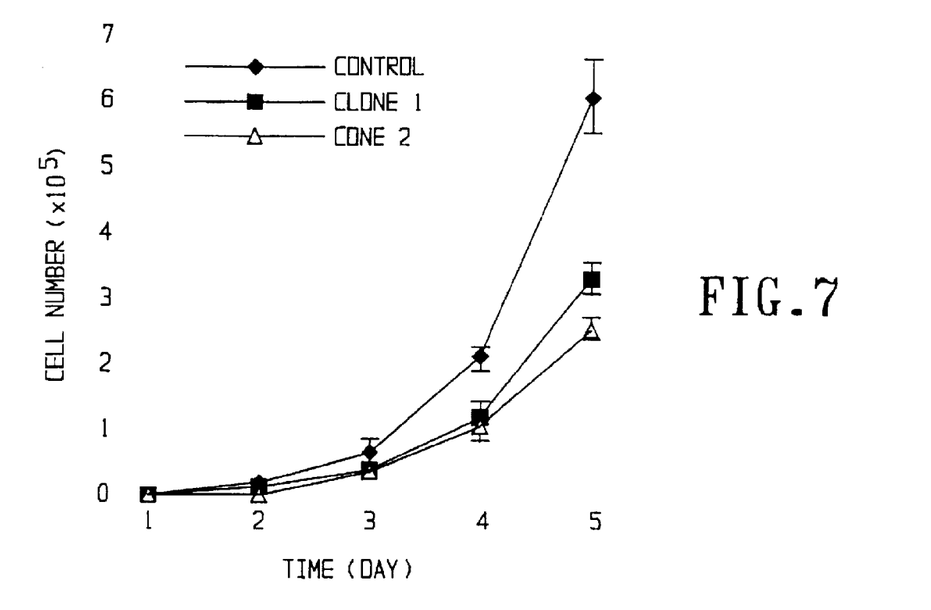
FIG. 7: Effect of ERRP cDNA transfection on proliferation of HCT-116 cells. The control (vector-transfected) and ERRP cDNA transfected cells were maintained in DMEM/ 10% FBS. Each value represents mean ±SEM for 6 observations.

To determine putative functional properties of ERRP, the rate of proliferation of ERRP-expressed cells (Clones #1 and 2) was compared with control cells. Results from a 5-day cell culture study revealed that although cells from all three clones grew essentially at the same rate during the first 3 days, the rate of proliferation in ERRP transfected cells decreased markedly during the next two days in culture when compared with controls as is shown in FIG. 7. To demonstrate that the inhibition of HCT-116 cell proliferation by ERRP expression was not due to a "positive effect" of the inserted DHA, we assayed three other distinct ERRP-transfected HCT-116 cell subclones. Each of these subclones exhibited decreased proliferation relative to controls.

Figure 8:
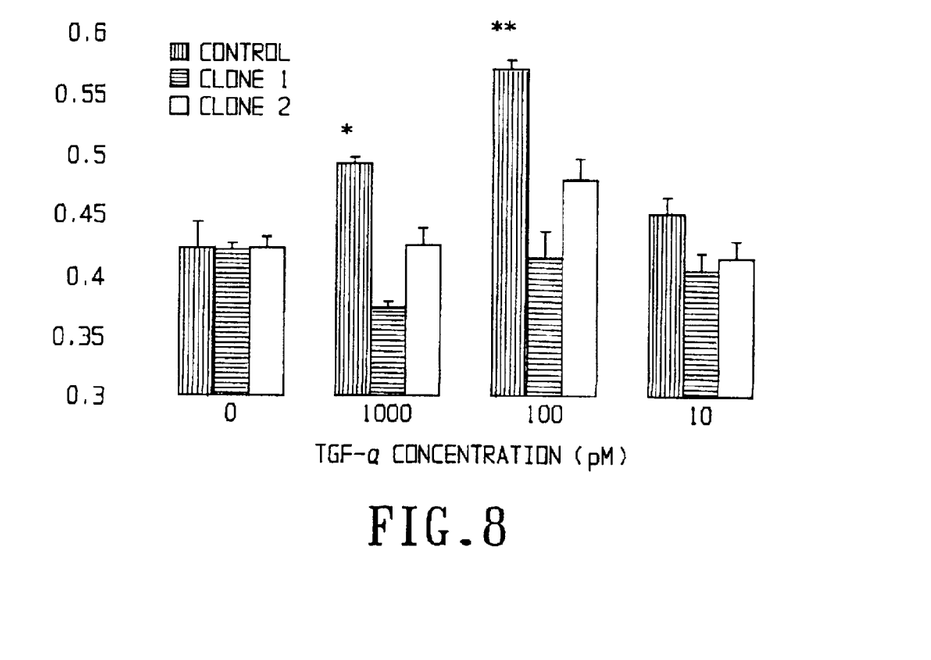
FIG. 8: Effects of increasing concentrations of TGF-α on proliferation of ERRP cDNA or vector-transfected HCT-116 cells. Values represent mean ±SEM for 6.

TGF-α-induced proliferation of ERRP transfected and control HCT-116 cells was examined. In this investigation, 48 h serum-starved (0.1% FBS) cells from clones 1 and 2 as well as those from the vector-transfected clone were maintained for 24 h in the absence (basal) or presence of increasing concentration of TGF-α ($10^{-11}$ to $10^{-9}$M). Results revealed that whereas TGF-α at a dose of either $10^{-9}$ or $10^{-10}$M significantly stimulated proliferation in control cells, it had no effect on cells from either clone 1 or clone 2 as is shown in FIG. 8.

Figure 9:
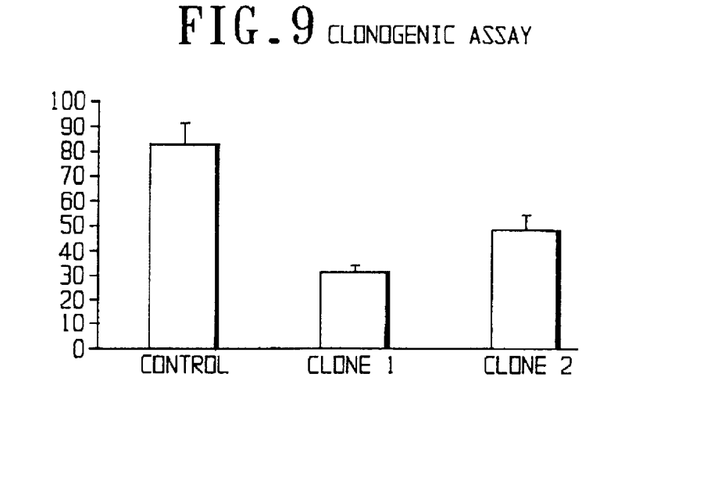
FIG. 9: Clonogenic assay in soft agar showing changes in proliferation of HCT-116 following transfection with either ERRP cDNA (clones 1 and 2) or the vector only (controls). One milliliter containing 100 cells were sandwiched between 1.8% and 0.3% agarose in DMEM/10% FBS. Plates were incubated at 37° C. for 14 days. Values represent mean ±SEM of 6 observations.
Figure 10:
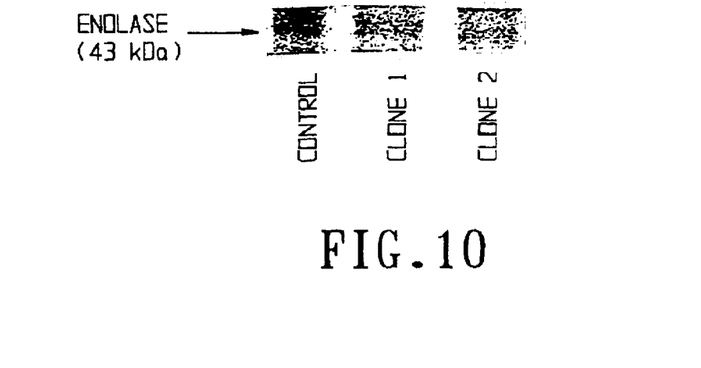
FIG. 10: Illustration of the changes in EGF-R tyrosine kinase (Tyr-K) actively in HCT-116 following transfection with ERRP cDNA (clones 1 and 2). Control cells were transfected with the vector.

To determine whether transfection of ERRP in HCT-116 cells will affect the tumorigenic property of this cell line, extent of proliferation of clones 1 and 2 and their control counterpart (vector transfected cells) was examined in soft agar over a period of 14 days. As shown in FIG. 9, transfection of ERRP in HCT-116 cells markedly decreased their ability to grow in soft agar. Number of colonies formed by clones 1 and 2 were 65% and 40% lower, respectively, compared to the control clone. Size of the colonies formed by clone 1 or 2 was also found to be considerably smaller than those formed by the vector-transfected control clone.

Figure 14:
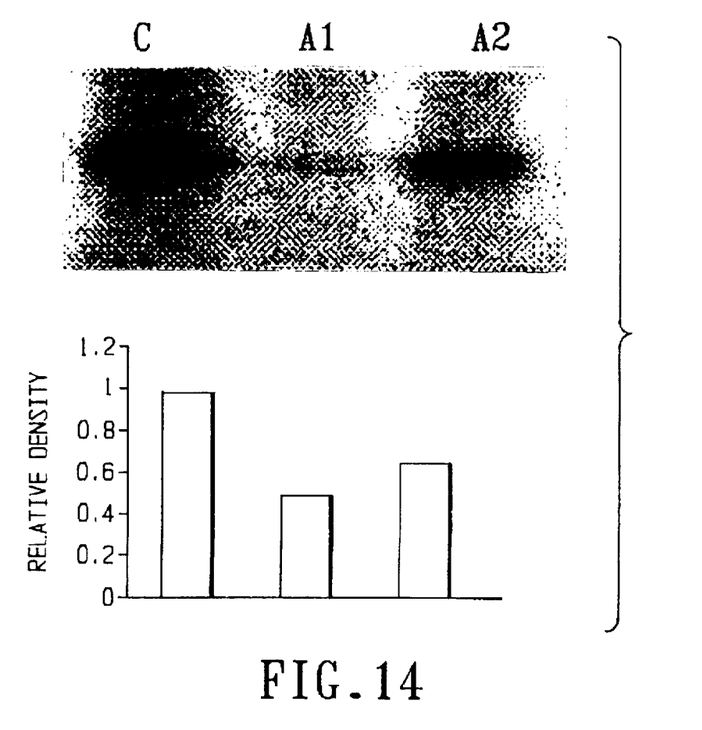
FIG. 14: Autoradiograph showing changes in the activation of EGF-R tyroisne kinase in HCT-116 cells following transfaction with ERRP cDNA (clones 1 and 2, marked as A1 and A2) or the vector only (control) as determined by the extent of phosphophylation of acid-denatured enolase. The cell maintained in DMEM cell medium containing 0.1% FBS.

To examine the antiproliferative effect of ERRP by the inhibition of the intrinsic tyrosine kinase activity of EGF-R. As is shown in FIG. 14 basal EGF-R tyrosine kinase activity in ERRP-overexpressed HCT-116 cells (clones 1 and 2) was about 50–60% below the control cells.

Figure 15:
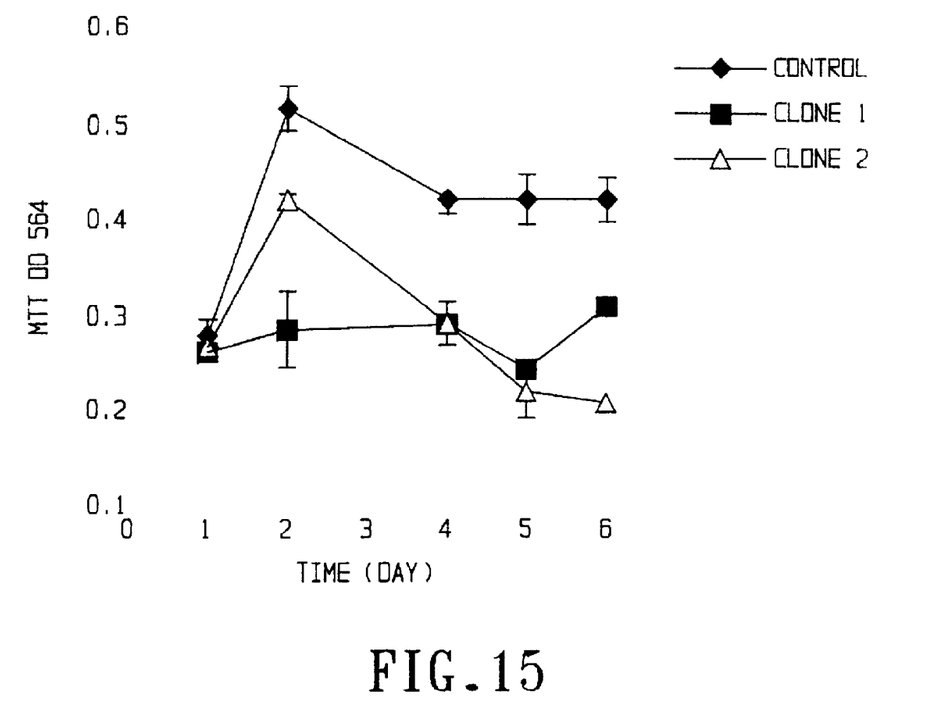
FIG. 15: Effect of serum starvation (0.1% FBS) on proliferation of ERRP-overexpressed (clones 1 and 2) and vector transfected (control) HCT-116 cells.

Serum starvation also resulted in a marked 50–70% inhibition in proliferation of ERRP-transfected HCT-116 cells (clones 1 and 2) compared to the vector-transfected control cells as seen in FIG. 15.

Figure 11:
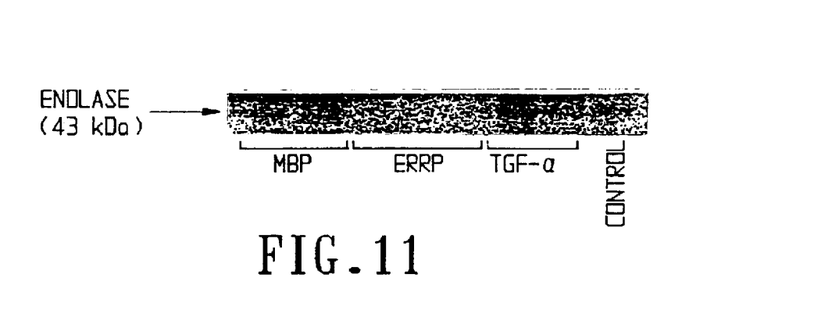
FIG. 11: Illustration of the effect of ERRP-fusion protein on EGF-R Tyr-K activity in HCT-116 cells. Cells were exposed to either 5 µg of ERRP fusion protein bound to MBR or MBP alone for 5 minutes at 37° C.

The role of ERRP in regulating EGF-R Tyr-K activity was determined by raising an ERRP fusion protein in E. coli. Purified ERRP-fusion protein was bound to its carrier MBP (molecular binding protein, then utilized to study its effects on EGF-R Tyr-K activity in HCT-116 cells, as seen in FIG. 11. When HCT-116 cells were exposed to 5 μg of MBP-bound ERRP for 5 minutes at 37° C. a marked reduction (80–90%) in EGF-R Tyr-K activity was observed when compared to HCT-116 cells exposed to either MBP alone or to control cells.

Figure 12:
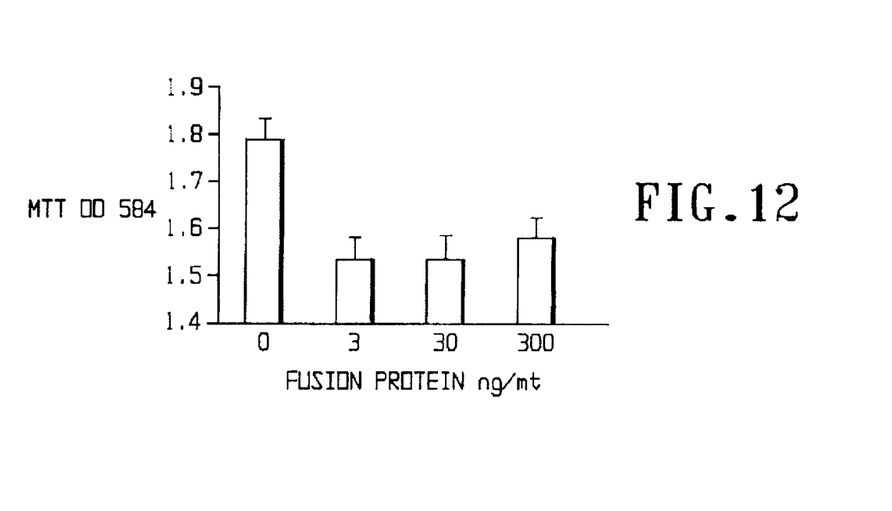
FIG. 12: Comparison of the effects of ERRP-fusion protein of proliferation of HCT-116 cells. Cells were exposed to a concentration of 3, 70 and 300 ng/ml of ERRP fusion protein for 48 hours.

The antiproliferation effect of ERRP-fusion protein was determined by exposing HCT-116 cells to ERRP-fusion protein for 48 hours. As is seen in FIG. 12, exposure of HCT-116 cells to the ERRP fusion protein for 48 hours reduced proliferation by 25–30% compared to control cells.

Figure 13:
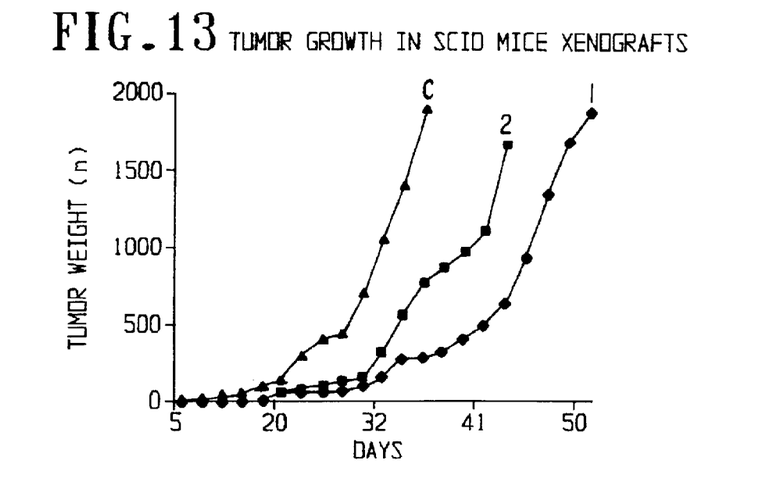
FIG. 13: Tumor growth in SCID mouse xenografts showing the difference in the rate of growth of tumors formed by HCT-116 cells, transfected with ERRP cDNA (clones 1 and 2) or the vector only (control).

To determine the tumorigenic properties of ERRP, the growth rate of tumors-induced by HCT-116 cells, was examined in SCID mouse xenografts. Groups of SCID mice were injected with either $5 \times 10^6$ HCT-116 cells (clone 1 or 2) per flank or $5 \times 10^6$ HCT-116 cells (control, transfected with vector) per flank. Tumor growth was monitored and when the tumor(s) attained the size of approximately 1800 mg, the mice were killed. It was observed that in mice injected with control cells, the tumor(s) attained the required weight on the $24^{th}$ day after injection, whereas with clone 1 or 2, it took 14–16 days longer for tumor(s) to grow to that size as is seen in FIG. 13. Tumor growth was slowest for clone 1 transfected cells as was colony formation in soft agar.

The ERRP was isolated and characterized and the fusion protein made in the following example.

Methods

Isolation of RNA: Total RNA was isolated from different tissues and colon carcinoma cell line HCT-116 utilizing RNA-STAT solution (Tel-Test, Friendswood, Tex.) according to the manufacturer's instruction. P, poly A+ was isolated from total RNA by oligo(dT) cellulose chromatography according to the instructions provided by GIBCO-BRL (Gaithersburg, Md.).

Construction of cDNA expression library and screening: Poly A+ RNA, isolated from mucosal scrapings from the gastro-duodenal region of the gastrointestinal tract was utilized for this purpose. An unamplified cDNA expression library was constructed using the EcoRI cloning sites of the λg11 vector system in Y1090r-strain according to the conditions recommended by Stratagene (La Jolla, Calif.). The ligated vector-insert was packaged using Giga-Pack bacterial extracts supplied by Stratagene. The library thus constructed contained 3×10⁶ pfu (plaque forming units) per ml. Non-recombinant phage associated with the library was about 4%. The reason for constructing an unamplified mucosal library was to minimize the analysis of identical positive clones.

Six duplicate IPTG-treated nitrocellulose filters containing the imprint of 50,000 plaques were washed with PBS-0.1% Tween-20, and left in a blocking buffer (PBS containing 7% nonfat dry milk, 0.5% BSA and 0.1% Tween-20). Membranes were then washed at room temperature in PBS-0.1% Tween-20, and subsequently incubated for 2 h at room temperature with pp55 antibodies (1:5000 final dilution) which were pre-adsorbed six times with *E. coli* lysate protein according to the protocol provided by Stratagene. Bound antibody was visualized by the enhanced chemiluminescence (ECL) detection system (Amersham) according to the manufacturer's instruction.

Sequence analysis: DNA from one of the positive plaques (referred to here as ERRP) was isolated and purified. Restriction analysis by EcoRI showed its size to be about 1.6 kb. This was subcloned into EcoRI sites of pBluescript (KS+) vector and subsequently sequenced by the dideoxy chain termination method at the Core Facility of the Center for Molecular Medicine and Genetics, Wayne State University, Detroit. The nucleotide sequence, thus obtained, was compared with known sequences in GenBank using the NCBI BLAST search program.

Rapid Amplification of cDNA Ends (RACE): Since the candidate cDNA under study lacked the termination codon, RACE was utilized to obtain the 3' end in the following manner. Briefly, 1 µg Poly A⁺ RNA from rat small intestinal mucosa was heat denatured at 65° C. for 3 min and reverse transcribed into a single strand cDNA according to the instruction provided by GIBCO-BRL (Gaithersburg, Md.) in a 20 µg reaction mixture [50 mM Tris-HC1, pH 8.15,1 mM each dNTP, 10 mM dithiothreitol, 6 mM MgCl₂ 40 mM KC1, 10 U Rnasin (Promega, Madison, Wis.) 10 U AMV reverse transcriptase (GIBCO-BRL)], with 0.5 µg of oligo-dT primer [5'GACTCGAGTCGACATCGATTTTTTT-TTTTTTTTTT-3'] (SEQ. ID NO: 3) containing XhoI, SalI, and ClaI restriction sites. The mixture was incubated at 41° C. for 2 h and the product was subsequently used for amplification of 3'-end of 1.6 kb fragment of ERRP. The reaction mixture in 50 µl contained: 1 µl of first strand cDNA, 3'-end primer [5'-CGCACTCCTCC-TCTAGACCCAC-3'] (SEQ. ID NO: 4) and (dT) 17-adaptor [25 pmol each], 10% dimethylsulfoxide, 1.5 mM of each dNTP. The mixture was heat denatured for 5 min at 95° C., annealed for 2 min at 53° C. in the presence of 2.5 U of Taq DNA polymerase followed by extension for 40 min at 75° C. The PCR reaction for amplification was carried out for 40 cycles using the step program (denaturation at 94° C. for 40 sec; annealing at 53° C. for 2 min and extension at 72° C. for 3 min) followed by a 15 min final extension at 72° C.

The PCR products from above were directly ligated into pCRII vector (TA cloning kit, Invitogen Corp.), followed by transformation of electro-competent *E. Coli* DH5α cells with one tenth (¹⁄₁₀ᵗʰ) of the ligation DNA. Approximately 10,000 independent bacterial colonies were screened by colony hybridizaton methodology using PCR amplified 3' end of ERRP cDNA (SEQ. ID NO. 1) (from positions 1444 to 1578) as probe. Several independent colonies were identified, followed by the secondary screening in order to obtain purified plasmids.

Northern-blot analysis Aliquots of one microgram of poly A⁺ RNA isolated from different tissues were electrophoresed in a 1.5% agarose gel containing 2.2 M formaldehyde. After electrophoresis, RNA was transferred to a nylon or nitrocellulose membrane by capillary blotting and subsequently exposed to an UV cross-linker (Strategene, La Jolla, Calif.) for 30 sec (autocross) and prehybridized in 5×SSC (1×SSC, 0.15 M sodium chloride, 0.015 M sodium citrate) containing 2% blocking reagent (Boehringer-Mannheim), 50% formamide and 0.1% sodium lauroylsarcosine and 0.02% sodium dodecyl sulfate (SDS) for 2 h at 50° C.

Hybridization with ³²P-labeled RNA probe of 1.5 kb cDNA under study was performed for 18 h at 50° C. in the same solution. The plasmid pBK containing 1.6 kb cDNA was linearized by digesting with Pstl. The antisense RNA probe was then synthesized using 1 µg of linearized plasmid with T3 RNA polymerase with the use of a commercial kit (StripAble RNA, Ambion, Austin, Tex.). Glyceraldehyde-3-phosphate dehydrogenase (GAPDH) was used as an internal control. GAPDH RNA probe was prepared by transcribing 1 µg of pTR1-GAPDH (rat; Ambion) with T3 RNA polymerase. The probes were labeled with [(α-³²P]UTP according to the manufacturer's instructions.

Stable transfection of ERRP and Cell Culture: The cDNA 1.6 kb under study, which was subcloned in pBluescript (KS+) vector, was digested with Pvu II followed by EcoR I. The resultant fragment was inserted into EcoRI/EcoRV cloning sites of the eukaryotic expression vector pcDNA 3.1 (+) containing neomycin-resistant gene [Invitrogen]. The resultant construct and the vector DNA (without cDNA insert) were used to stably transfect a human colon cancer cell line HCT-116.

HCT-116 cells, maintained in Dulbecco's modified Eagle's medium (DMEM) supplemented with 10% fetal bovine serum (EBS), 100 U/ml streptomycin-penicillin and 0.25 µg/ml amphotericin B, were transfected with either 1.6 kb portion of the 1.8 kb full-length ERRP cDNA or the vector alone (control) by lipofectin according to the manufacturer's instruction (GIBCO-BRL) in the presence of neomycin (geticin, G418; GIBCO-BRL). Neomycin-resistant colonies were selected in the presence of 0.6 mg/ml G418. Colonies were picked at random and grown as individual cell lines in the presence of 0.4 mg/ml G418. Each cell line was subjected to RT-PCR analysis according to our standard protocol. Briefly, 3 µg of total RNA was reverse transcribed into first strand cDNA in a 20 µl reaction mixture containing: 2 µl 10×PXR buffer, 5 mM MgCl₂, 1 mM of each dNTP, 20 U RNAse inhibitor, 2.5 µM of Oligo (dT)₁₆ and 2.5 MuLV reverse transcriptase. The reaction mixture was incubated at room temperature for 10 min followed by incubations at 42° C. for 30 min, 95° C. for 5 min. and finally 5° C. for 5 min. First strand cDNA thus obtained was used for PCR analysis utilziing Amplitaq DNA polymerase (Perkin Elmer) and 0.15 µM of upstream primer [5'-CGCACTCCTCCTCTAGACCCAC-3'] (SEQ. ID NO: 5) (taken from ERRP sequence) and 0.15 µM downstream primer [5'ATTAACCCTCACTAAAGGGA3'] (SEQ. ID NO: 6) taken from pcDNA 3.1 (+) vector, and/or GAPDH upstream [5'-ACCACAGTCCATGCCATCAC-3'] (SEQ. ID NO. 7) and downstream primers [5-TCCAC-CACCCTGTTGCTGTA-3'] (SEQ. ID NO. 8). The PCR reaction for amplification was carried out for 35 cycles using a step program (denaturation at 95=C. for 1 min; annealing at 63° C. for 1 min and extension at 72° C. for mm followed by a 15 min. final extension at 72° C. The reaction product was electrophoresed on an 1.5% agarose gel, subsequently stained with ethidium bromide.

Tyrosine kinase activity of EGFR: The enzyme activity was determined in lysed cells according to our standard protocol. Briefly, plated cells were lysed in lysis buffer [50 mM tris-HC], pH 7.4, 100 mM NaCl, 2.5 mM EDTA, 1% Triton X-100, 1% Nonidet P-40, 2.5 nM $Na_3VO_4$, 25 μg/ml aprotinen, 25 μg/ml leupeptin and 50 μg/ml soybean trypsin inhibitor] using a Dounce homogenizer The homogenate was stirred in a mechanical rotator for 30 min at 4° C. and subsequently centrifuged at 10,000×g for 10 min at 4° C. Supernatant was assayed for protein content using the Bio-Rad protein assay kit (Bio-Rad, hercules, Calif.). Aliquots of cell lysate containing 1 mg protein were incubated overnight at 4° C. with 1 μg polyclonal antibody to EGFR (Santa Cruz Biotechnology, Santa Cruz, Calif.). The immune complexes were precipitated with Sepharose bound protein-G, washed several times with kinase buffer (25 mM HEPES, pH 7.5, 5 mM $MnCl_2$, 2.5 mM $MgCl_2$, 0.5 mM, ditheothreitol, 0.5 mM $Na_3VO_4$, 10 mM p-nitrophenol phosphate, 5 mM β-glycerol phosphate). The immunoprecipitates were resuspending in 30 μl kinase reaction buffer [HEPES, pH 7.5, 10 mM $MnCl_2$, 2.5 mM $MgCl_2$, 0.1 M Nacl 150 mM Ncl, 0.5 mM ditheothreitol, 0.5 mM $Na_3VO_4$, 10 mM p-nitrophenol phosphate, 5 mM β-glycerol phosphate and 0.1 mM ATP] and assayed for tyrosine kinase activity by measuring $^{32}$incorporation from [γ-$^{32}$P]ATP into acid-denatured enolase.

What is claimed is:

1. An isolated polynucleotide comprising the nucleotide sequence of SEQ ID NO 1.

2. The isolated polynucleotide of claim 1, comprising a sequence that encodes polypeptide comprising the amino acid sequence of SEQ ID NO: 2.

3. The isolated polynucleotide of claim 1, wherein the polynucleotide encodes for a polypeptide having inhibitory activity on cell proliferation.

4. The isolated polynucleotide of claim 3, wherein the polypeptide possesses the property of inhibiting epidermal growth factor receptor (EGFR).

5. An isolated polynucleotide comprising a sequence that encodes a polypeptide comprising the amino acid sequence of SEQ ID NO 2.

6. The isolated polynucleotide of claim 5, wherein the polypeptide is part of a fusion protein.

7. An expression vector comprising the polynucleotide of SEQ ID NO: 1.

8. A host cell line stably transfected with the expression vector of claim 7.

9. The host cell line of claim 8, wherein the cell line is human colon cancer cell line HCT-116.

10. A method for producing a polypeptide comprising the amino acid sequence of SEQ ID NO: 2, comprising the steps of:

culturing the host cell of claim 8 under conditions suitable for expression of the polypeptide; and recovering the polypeptide from the host cell culture.

11. A method for transfecting a cell line with a vector encoding for an epidermal growth factor receptor related protein (ERRP) comprising the steps of:

subcloning a cDNA sequence of SEQ ID NO 1 into a pBluescript KS+vector;

digesting said pBluescript KS+vector with Pvull, followed by EcoRI;

inserting a resulting fragment into EcoRI/EcoRV cloning sites of eukaryotic expression vector pcDNA 3.1(+) to form a resultant construct; and transfecting said cell line with the resultant construct.

12. The method of claim 11, wherein said cell line is a human cell line.

* * * * *